United States Patent [19]

Magó neé Karácsony et al.

[11] 4,101,552

[45] Jul. 18, 1978

[54] NOVEL LYSERGIC ACID AMIDES AND PROCESS FOR PREPARING SAME

[75] Inventors: Erzsébet Magó née Karácsony; József Borsi; László Tardos; Ildikó Király; Sandor Elek; István Elekes, all of Budapest, Hungary

[73] Assignee: Richter Gedeon Vegyeszeti Gyar Rt., Budapest, Hungary

[21] Appl. No.: 679,866

[22] Filed: Apr. 23, 1976

[30] Foreign Application Priority Data

Apr. 24, 1975 [HU] Hungary .................. GO 1309

[51] Int. Cl.$^2$ .................. C07D 457/06; A61K 31/48
[52] U.S. Cl. .................. 260/285.5; 424/261
[58] Field of Search ...................... 260/285.5

[56] References Cited

U.S. PATENT DOCUMENTS

| 2,090,430 | 8/1937 | Stole et al. | 260/285.5 |
| 2,736,728 | 2/1956 | Pioch | 260/285.5 |
| 2,997,470 | 8/1961 | Pioch | 260/285.5 |
| 3,583,992 | 6/1971 | Hofmann et al. | 260/285.5 |
| 4,005,089 | 1/1977 | Mago et al. | 260/285.5 |

Primary Examiner—Donald G. Daus
Assistant Examiner—Mary C. Vaughn
Attorney, Agent, or Firm—Young & Thompson

[57] ABSTRACT 9,10-Dihydrolysergic acid-(3'-/pyrrolid-2"'-on-1'-yl/-propyl)-amide, 1-methyl-9,10-dihydrolysergic acid-(thiazoline-2'-yl)-amide and lysergic acid-(3'-allyloxy-2'-oxy-propyl)-amide and their pharmaceutically acceptable acid addition salts possess antihypertensive and antiserotonin effect and exert an action on the central nervous system.

2 Claims, No Drawings

NOVEL LYSERGIC ACID AMIDES AND PROCESS FOR PREPARING SAME

The present invention relates to novel lysergic acid amides selected from the group consisting of 9,10-dihydrolysergic acid-(3'-/pyrrolid-2''-on-1'-yl/-propyl)-amide, 1-methyl-9,10-dihydrolysergic acid-(thiazoline-2'-yl)-amide and lysergic acid-(3'-allyloxy-2'-oxypropyl)-amide and their pharmaceutically acceptable acid addition salts. The compounds according to the present invention possess antihypertensive and antiserotonin effect and exert an action on the central nervous system.

It is known that all naturally occurring ergot alkaloids are lysergic acid amides and have played for decades an important role in therapy. Research aiming at semi-synthetic derivatives starting from lysergic acid is mainly concerned with the preparation of lysergic acid amides.

The Hungarian patent specification Nos. 155,942, 156,385 and 164,051 describe compounds similar to those of the general formula I of the present invention, but have a structure different from that of the compounds of the general formula I.

The object of the present invention is to provide novel lysergic acid amides having a significant physiological action.

In compliance with the process according to the invention the novel lysergic acid amides and their acid addition salts can be prepared by reacting the corresponding carboxylic acid with the desired amine and, if desired methylating and/or hydrogenating the obtained product, and, if desired, converting the product with a physiologically acceptable acid into an acid addition salt.

As reactive derivatives of the acid, preferably acid anhydrides formed with trifluoroacetic acid or sulphuric acid, acid chlorides or hydrochlorides, azides, and active esters, preferably the pentachlorophenyl esters, can be used.

A preferable method of implementing the process according to the invention consists in suspending the lysergic acid in a mixture of methylene chloride and acetonitrile and reacting it in the presence of dicyclohexyl-carbodiimide with pentachlorophenol, then reacting preferably without separation the obtained lysergic-(pentachlorophenyl)-ester with the desired amine. The obtained product is purified by recrystallization and, if desired, by column chromatography and if desired, converted into an acid addition salt. Primarily maleic acid and hydrochloric acid can be used as salt-forming acids.

One can proceed also by reacting the lysergic acid with trifluoroacetic acid anhydride in the presence of trifluoroacetic acid in an inert solvent or in a solvent mixture and then reacting the thus-obtained mixed anhydride in an inert solvent or in the presence of a tertiary organic base with the desired amine.

According to another preferred method of preparation the acid is converted into its hydrazide, then the azide is prepared with sodium nitrite in an aqueous dioxane solution, and then the azide is reacted with the amine.

One can proceed also by preparing from the acid in an inert solvent with phosphorus pentachloride the acid chloride, hydrochloride and reacting the latter in the presence of a tertiary organic base in an inert solvent with the amine.

According to Hungarian patent specification No. 161,090 the double bond $\Delta^9$ can be hydrogenated at any stage of the process in an alkaline metal - ammonia system, using isopropanol as proton donor and beside ammonia as a second solvent. The N-methylation of the products prepared in the above way can preferably be carried out by reduction with a large excess of alkaline metal and after the completion of the reduction converting the excess alkaline metal into an alkaline metal amide by any of the known methods, and then adding methyl iodide to the reaction mixture.

Hydrogenation can be performed also by catalysis, using palladium on charcoal, Raney nickel or platinum oxide as catalyst in an inert solvent.

The compounds according to the invention exert a valuable action on the central nervous system and have also an antiserotonin and antihypertensive effect.

When investigating the antidepressant-type compounds of the present invention it has been found that similarly to the tricyclic antidepressants, these compounds too inhibit to a significant degree the hypothermic and neurodepressive action of reserpine, and some of these compounds are more potent than Imipramine [5-(3-dimethylaminopropyl)-10,11-dihydro-5H-dibenz(b,f)azepine] while the toxicity of these compounds is low (Table 1). It is further characteristic of the antidepressant nature of these compounds that they potentiate the psychostimulant action of Amphetamine (1-phenyl-2-aminopropane) and the hypertensive action of noradrenaline.

The currently used drugs in therapy display their depression-inhibiting action after a period of latency of several weeks; hence the compounds according to the invention have a considerable advantage inasmuch as their effect appears at lower dose levels than that of the tricyclic antidepressants and it develops more rapidly.

One of the compounds of the present invention possesses in vitro and in vivo a specific antiserotonin effect (Table 2). In vitro very low concentrations of the compound inhibit on the rat uterus the contraction of smooth muscles induced by serotonin. The compound was found to inhibit in vivo the development of serotonin oedemas. It is characteristic of the compound that its effect is well measurable even after oral administration, indicating its ready peroral absorption. The 1-methyl-9,10-dihydrolysergic-acid-(2'-thiazolin-2'-yl)-amide bimaleate has a particularly favourable peroral efficacy (Example 4), its peroral $ED_{50}$ value being 0.120 mg per kg of body weight, thus considerably (about 3.5 times) surpassing the efficacy of Deseryl (N-[1-(hydroxymethyl)propyl]-1-methyl-d-/+/-lysergamide).

It is characteristic of one of the compounds of the present invention and having a hypotensive action that when administered in intravenous doses of 0.1 to 0.5 mg/kg to cats and dogs in pentothal anaesthesia it provokes a permanent decrease of 20 to 60 mmHg in blood pressure (Table 3). The compound tends to improve renal circulation, but does not cause a constriction of the cerebral blood-vessels or a substantial change in the blood-vessels of other organs. It inhibits hypertension produced by the stimulation of the baroreceptors and the central vagus stump. It also inhibits acute hypertension produced by the infusion of angiotensin. The compound has no alpha- or beta-sympatholytic, ganglion-blocking or adrenergic neuron-blocking action and does not alter the catecholamine content of the organs. It might therefore be assumed that the hypotensive effect of the compound according to the invention is the result of its inhibiting effect on the sympathetic cerebral centres. These properties are the most characteristic of the dihydro-lysergic-acid-(3'-/pyrrolid-2''-on-1''-yl/-propyl)-amide bimaleate (Example 1).

Table 1

Antidepressant effect ($\Delta t$, °C) and acute toxicity ($LD_{50}$)
Antidepressant test: antagonization of reserpine hypothermia
Dose: 30 mg/kg, intraperitoneally
$\Delta t$, °C: change in body temperature compared to that of the control
Description of the method: ASKEW, B.M., Life Sci. 10, 725 (1963).
Acute toxicity: $LD_{50}$ on mice after 24 hours.
Description of the method: LITCHFIELD, J.T.jr. and WILCOXON, F.J., Pharmacol. exp. Ther. 96, 99 (1949).

| Number of compound | $\Delta t$, °C | $LD_{50}$, mg/kg intraperitoneally | orally |
|---|---|---|---|
| 2 | 3.5 | 100< | 100< |
| 4 | 4.1 | 330.0 | 315.0 |
| 5 | 3.6 | 100< | 100< |
| 6 | 5.4 | 110 | 205 |
| 7 | 8.0 | 100< | 100< |
| 9 | 4.7 | 100< | 100< |
| 10 | 3.9 | 100< | 100< |
| 11 | 2.9 | 100 | 100< |
| 12 | 6.9 | 30 | 100 |
| 13 | 7.0 | 100< | 100< |
| 14 | 3.4 | 100< | 100< |

Table 2

Antiserotonin effect

*In vitro:* on isolated rat uterus
Description of the method: GADDUM, J. H. and HAMMED, L. A.: Brit. J. Pharmacol. 9, 240 (1954).
*In vivo:* rat-sole oedema
Oedema produced by a standard dose of serotonin creatinine sulphate: 5 μg per sole in 0.1 ml
Descriptin of the method: BONTA, I. L.: Arch. int. Pharmacodyn. 132, 147 (1961).

| Number of compound | *In vitro* $ED_{50}$, g/ml | Serotonin oedema blocking effect $ED_{50}$ mg/kg subcutane | peroral |
|---|---|---|---|
| 3 | $5 \times 10^{-9}$ | 0.3 | 1.5 |
| 4 | $5 \times 10^{-11}$ | 0.022 | 0.120 |
| 5 | $5 \times 10^{-7}$ | 0.3 | 3.0 |
| 9 | $5 \times 10^{-7}$ | 0.03 | 1.0 |
| 14 | $5 \times 10^{-10}$ | 0.3 | 3.0 |
| Deseryl | $5 \times 10^{-y}$ | 0/026 | 0.640 |

Table 3

Antihypertensive effect

Method: the blood pressure of cats anaesthetized with intraperitoneally administered 30 mg/kg of pentobarbital was measured in the left femoral artery by means of the Statham P 23 db manometer and recorded on Hellige polygraph. The compounds were administered into the right femoral vein.
Number of animals: 2 to 5 per dose.

| Number of compound | Dose mg/kg i.v. | Decrease in blood pressure mmHg | duration hours |
|---|---|---|---|
| 2 | 0.5 | −50 | 1.5 |
| 3 | 0.5 | −30 | 2.0 |
| 8 | 0.5 | −50 | 2. |
| 9 | 1.0 | −20 | 1.5 |
| Dihydro-ergot-amine | 0.1 | — | — |
|  | 0.2 | −25 | 0.5 |

Reference: MCLEOD, L.J.: Pharmacological Experiments onIntact Preparations,Livinstone, 1970, pp. 65–66.

The compounds of the invention can be converted with therapeutically acceptable additives into pharmaceutical preparations.

The following non-limiting Examples shall serve to further illustrate the compounds according to the invention and their preparation.

EXAMPLE 1

9,10-Dihydrolysergic-acid-(3'-/pyrrolid-2''-on-1'''-yl/-propyl)-amide bimaleate 5.39 g of 9,10-dihydrolysergic-acid-(pentachlorophenyl)-ester prepared according to Hungarian patent specification No. 163,534 are dissolved under constant stirring in 100 ml of anhydrous chloroform, and 1.42 g of N-(3'-aminopropyl)-pyrrolid-2-one dissolved in 10 ml of chloroform are added dropwise under cooling with icy water. The solution is stirred at room temperature for 1 hour and then shaken with 6×25 ml of a 1% solution of tartaric acid in water. The extracts are united and the pH is adjusted to 8 by the addition of a few ml of a 10% ammonium hydroxide solution. The aqueous solution is shaken with 5×50 ml of chloroform. The chloroform fractions are united, dried with sodium sulphate, filtered and evaporated under vacuum. The residue is dissolved in ethanol and a salt is formed with maleic acid. The obtained 4.12 g (80%) of 9,10-dihydrolysergic-acid-(3'-/pyrrolid-2''-on-1'''-yl/-propyl)-amide bimaleate melts at 174°–176° C. $(\alpha)_D^{20} = -42.0$ (c = 0.5, in 50% aqueous ethanol).

EXAMPLE 2

Lysergic-acid-(3'-/pyrrolid-2''-on-1'''-yl/-propyl)-amide bimaleate

The title compound is prepared from 5.37 g of lysergic-(pentachlorophenyl)-ester and 1.42 g of N-(3'-aminopropyl)-pyrrolid-2-one according to the method given in Example 1. The obtained 3.75 g (70%) of lysergic-acid-(3'-/pyrrolid-2''-on-1'''-yl/-propyl)-amide bimaleate melts at 171°–173° C. $/\alpha/_D^{20} = +56.1$ (c = 0.5, in 50% aqueous ethanol).

EXAMPLE 3

1-Methyl-9,10-dihydrolysergic-acid(3'-/pyrrolid-2''-on-1'''-yl/propyl)-amide bimaleate The title compound is prepared from 5.53 g of 1-methyl-9,10-dihydro-lysergic-(pentachlorophenyl)-ester and 1.42 g of N-(3'-aminopropyl)-pyrrolid-2-one according to the method given in Example 1. The obtained 3.9 g (75%) of 1-methyl-9,10-dihydrolysergic-(3'/pyrrolid-2''-on-1'''-71/-propyl)-amide bimaleate melts at 115°–117° C. $/\alpha/_D^{20} = -47$ (c = 0.5, in 50% aqueous ethanol).

EXAMPLE 4

1-Methyl-9,10-dihydrolysergic-acid-(2'-thiazolin-2'-yl)-amide bimaleate a. Preparation of 1-methyl-9,10-dihydro-lysergic acid 20 g of metallic sodium are dissolved in 1.5 liters of liquid ammonia and after dissolution 25 ml of ethanol and 26.8 g of dried powdered lysergic acid are added. The reaction mixture is stirred at −40° C for 30 minutes. The progress of hydrogenation is followed by means of layer chromatography (on silica-gel plate with a 10:1:5 developing solution of chloroform, water and methanol. The hydrogenated product shows no fluorescence under UV light. When the reaction is over, anhydrous ethanol is added to the reaction mixture until the blue colour disappears and then a solution of 48 g of methyl iodide in 50 ml of anhydrous ether is added dropwise. The mixture is stirred for further 10 to 15 minutes and then evaporated to dryness under vacuum. The residue is moistened with 50 ml of ethanol and diluted with 150 ml of water. The pH of the solution is adjusted with acetic acid between 7 and 8 under cooling. 1-Methyl-9,10-dihydrolysergic acid is allowed to crystallize in the refrigerator for several days, then filtered, washed with water and dried under vacuum.

b. Preparation of 1-methyl-9,10-dihydrolysergic acid chloride hydrochloride 2.81 g of dried 1-methyl-9,10-dihydrolysergic acid (prepared according to step (a) are added slowly and under cooling to 3.5 g of phosphorus pentachloride dissolved in a mixture of 60 ml of acetonitrile and 60 ml of phosphorus trichloride. From the temporarily formed solution the formed 1-methyl-9,10-dihydrolysergic acid chloride hydrochloride precipitates on continued stirring. The suspension is stirred at 0° to 5° C for 30 minutes, then the reaction mixture is evaporated to dryness under vacuum, the residue suspended in 30 ml of tetrahydrofurane, filtered, the precipitate is repeatedly washed on the filter with petroleum ether and dried at 40° C under vacuum.

c. Preparation of 1-methyl-9,10-dihydrolysergic-acid-(2'-thiazolin-2'-yl)-amide bimaleate 1.78 g of 2-amino-2-thiazoline hydrochloride are dissolved in 200 ml of chloroform, and then 8.4 ml of anhydrous chloroform are added. The solution is cooled with icy water and 3.5 g of the 1-methyl-9,10-dihydrolysergic acid chloride hydrochloride prepared according to step (b) are added. The acetylating reaction is completed in one hour. The reaction mixture is evaporated to dryness at low temperature under vacuum, the residue suspended in 100 ml of a 1% aqueous sulphuric acid solution and 300 ml of chloroform, and the pH of the mixture adjusted to 8 by the addition of an aqueous ammonium hydroxide solution. After shaking the organic phase is separated and extraction is repeated with 4×50 ml of chloroform. The united organic phases are dried with sodium sulphate, filtered and evaporated to dryness under vacuum. The residue is purified by chromatography on a silica-gel column. For elution a 90:0.3:10 mixture of chloroform, water and ethanol is used. The salt is prepared from the purified product with alcoholic maleic acid. The obtained 3.05 g (66%) of 1-methyl-9,10-dihydrolysergic-acid-(2'-thiazolin-2'-yl)-amide bimaleate melts at 159° C. $/\alpha/_D^{20} = -85.4$ (c = 0.5, in 50% aqueous ethanol).

EXAMPLE 5

9,10-Dihydrolysergic-acid-(thiazolin-2'-yl)-amide bimaleate

The title compound is prepared from 2.7 g of dihydrolysergic acid and 1.7 g of 2-amino-2-thiazoline by the method given in step (c) of Example 4. The obtained 3.6 g (73%) of 9,10-dihydrolysergic-acid-(2'-thiazolin-2'-yl)-amide bimaleate melts at 174°-176° C. $/\alpha/_D^{20} = -53.4$ (c = 0.5, in 50% aqueous ethanol).

EXAMPLE 6

Lysergic-acid-(3'-allyloxy-2'-oxy-propyl)-amide bimaleate 100 ml of a solution containing 2.81 g of lysergic acid hydrazide in 0.1 N hydrochloric acid are added to 10 ml of a normal aqueous sodium nitrite solution, and 15 ml of N hydrochloric acid are added dropwise at 2° to 5° C under constant stirring. Stirring is continued for further 15 minutes while the temperature is kept between 0° and 5° C. The reaction mixture is neutralized with a saturated sodium hydrogen carbonate solution and extracted in 3 portions with a total amount of 2 liters of ether. The ether fractions are united, dried with anhydrous potassium carbonate, filtered, and a solution of 1.32 g of 3-allyloxy-2-oxypropylamine in 100 ml of isopropanol is added under constant stirring. Stirring is continued at room temperature for 4 hours. The reaction mixture is washed with water, then the aqueous phase extracted with 2×50 ml of chloroform and the united organic phases dried with anhydrous potassium carbonate and evaporated to dryness. The dry residue is dissolved in ethanol and a salt is formed with maleic acid. The obtained 3.6 g (72%) of lysergic-acid-(3'-allyloxy-2'-oxypropyl)-amide bimaleate melts at 184°-186° C. $/\alpha/_D^{20} = +47.9$ (c = 0.5, in 50% aqueous ethanol).

EXAMPLE 7

Lysergic-acid-(thiazol-2'-yl)-amide bimaleate 3.72 g of lysergic acid monohydrate are suspended in 20 ml of anhydrous acetonitrile and the suspension is cooled to −20° C under constant stirring. A solution of 5.46 g of trifluoroacetic acid anhydride in 20 ml of anhydrous acetonitrile is added dropwise so that the temperature is not allowed to rise above −20° C. After 10 minutes stirring at −20° C 1.3 g of aminothiazole are added to the clear solution and 20 ml of anhydrous pyridine are immediately added dropwise to the obtained suspension in such a manner as to prevent the rise of temperature above −10° C. The reaction mixture is stirred between −10° C and 0° C, for one hour, poured into 500 ml of chloroform and the pH adjusted to 8 by the addition of a 10% ammonium hydroxide solution. After shaking the aqueous phase is separated and extracted with 4×100 ml of chloroform. The united organic phases are dried with sodium sulphate and evaporated to dryness under vacuum. The last traces of pyridine are removed by the addition of 2×200 ml of toluene followed by distillation. The dry residue is purified by chromatography on a silica-gel column. A 90:1.5:25 mixture of chloroform, water and ethanol is used as eluent. From the purified product a salt is prepared with maleic acid in ethanol. The lysergic-acid-(thiazol-2'-yl)-amide bimaleate (4.0 g, 83%) melts at 148°-150° C. $/\alpha/_D^{20} = +71.6°$ (c = 0.5, in 50% aqueous ethanol).

EXAMPLE 8

9,10-Dihydrolysergic-acid-(thiazol-2'-yl)-amide bimaleate 1.8 ml of a palladium(II)-chloride solution prepared by dissolving 10 g of palladium(II)-chloride in a mixture of 30 ml of 2 N hydrochloric acid and 200 ml of water are mixed with a solution of 3.7 g of lysergic-acid-(thiazol-2'yl)-amide prepared according to Example 7 in 250 ml of 40% dioxane. Hydrogenation is performed at room temperature at a pressure of 60 atm under shaking till no more hydrogen is taken up by the mixture. The catalyst is removed from the mixture by means of filtration, the mixture evaporated under vacuum and 9,10-dihydrolysergic-(thiazol-2'-yl) amide is extracted from the concentrated solution with 6×100 ml of chloroform after the addition of 50 ml of aqueous sodium hydrogen carbonate. The chloroform phase is dried with sodium sulphate and evaporated under vacuum. The residue is dissolved in alcohol and the maleate salt is prepared with maleic acid. The obtained 4.1 g (85%) of 9,10-dihydrolysergic-(thiazol-2'-yl)-amide bimaleate melts at 169°–171° C. $/\alpha/_D^{20} = -54.4$. (c = 0.5, in 50% aqueous ethanol).

EXAMPLE 9

1-Methyl-9,10-dihydrolysergic-acid-(thiazol-2'-yl)-amide bimaleate

The title compound is prepared from 9,10-dihydrolysergic-(thiazol-2'-yl)-amide, prepared by the method given in Example 8, with sodium amide in anhydrous ammonia, then the sodium salt is reacted with methyl iodide. The crude product is purified by means of silica-gel column chromatography. The maleate salt is prepared with maleic acid in alcohol. The obtained 3.8 g (80%) of 1-methyl-9,10-dihydrolysergic-acid-(thiazol-2'-yl)-amide bimaleate melts at 118°–120° C. $/\alpha/_D^{20} = 68.2$ (c - 0.5, in 50% aqueous ethanol).

EXAMPLE 10

Lysergic-acid-(quinolin-5-yl)-amide bimaleate

The title compound is prepared from 2.81 g of lysergic acid hydrazide and 1.45 g of 5-aminoquinoline by means of the method described in Example 6. The obtained 3.7 g (70%) of lysergic-acid-(quinolin-5-yl)-amide bimaleate melts at 118°–120° C. $/\alpha/_D^{20} = +99.2$ (c - 0.5, in 50% aqueous ethanol).

EXAMPLE 11

Lysergic-acid-(1'-phenyl-pyrazol-5'-yl)-amide bimaleate

The title compound is prepared from 2.71 g of lysergic acid and 1.6 g of 1-phenyl-5-aminopyrazole by means of the method described in Example 7. The obtained 3.45 g (63%) of lysergic-acid-(1'-phenylpyrazol-5'-yl)-amide bimaleate melts at 170°–172° C. $/\alpha/_D^{20} = +79.7$ (c - 0.5, in 50% aqueous ethanol).

EXAMPLE 12

Lysergic-acid-(2'-fluoro-4'-methyl-phenyl)-amide bimaleate

The title compound is prepared from 5.37 g of lysergic-acid-(pentachlorophenyl)-ester and 1.3 g of 2-fluoro-4-aminotoluene by means of the method described in Example 1. The obtained 4.0 g (80%) of lysergic-acid-(2'-fluoro-4'-methyl-phenyl)-amide bimaleate melts at 203°–205° C. $/\alpha/_D^{20} = +54.4$ (c - 0.5, in 50% aqueous ethanol).

EXAMPLE 13

Lysergic-acid-(3'-methyl-mercapto)-anilide bimaleate

The title compound is prepared from 2.7 g of lysergic acid and 1.1 g of 3-(methyl-mercapto)-aniline by means of the method described in Example 7. The obtained 3.7 g (75%) of lysergic-acid-(3'-methyl-mercapto)-anilide bimaleate melts at 162°–164° C. $/\alpha/_D^{20} = +51$ (c - 0.5, in 50% aqueous ethanol).

EXAMPLE 14

1-Methyl-9,10-dihydrolysergic-acid-(4'-m-cresyl)-amide bimaleate

The title compound is prepared from 2.7 g of lysergic acid and 1.24 g of 4-amino-m-cresol by means of the method described in steps (a), (b) and (c) of Example 4. The obtained 3.4 g (68%) of 1-methyl-9,10-dihydrolysergic-acid-(4'-m-cresyl)-amide bimaleate melts at 144°–146° C. $/\alpha/_D^{20} = 57.0$ (c - 0.5, in 50% aqueous ethanol).

EXAMPLE 15

9,10-Dihydrolysergic-acid-(4'-m-cresyl)-amide bimaleate

The title compound is prepared from 2.7 g of 9,10-dihydrolysergic acid and 1.24 g of 4-amino-m-cresol according to the method described in step (c) of Example 4. The obtained 3.5 g (70%) of 9,10-dihydrolysergic-acid-(4'-m-cresyl)-amide bimaleate melts at 124°–126° C. $/\alpha/_D^{20} = -47.6$ (c = 0.5, in 50% aqueous ethanol).

EXAMPLE 16

9,10-Dihydrolysergic-acid-(3'-methylmercapto)-anilide bimaleate

To 2.75 g of 9,10-dihydrolysergic acid in a bomb tube 40 ml of 3-methylmercapto-aniline are added and the tube is closed under nitrogen atmosphere. The bomb tube is placed into a bath of 150° C and kept there protected against light for 10 hours. The reaction mixture is poured over 300 ml of icy water, and the pH of the solution is adjusted to 8 by the addition of acetic acid. 9,10-Dihydrolysergic (3'-/methylmercapto/)-anilide is extracted from the aqueous phase with 6×150 ml of chloroform. The united organic phases are dried with sodium sulphate, filtered and evaporated. The solvent-free residue is purified by chromatography on silica-gel column. A 40:30:10 mixture of chloroform, benzene and ethanol is used as eluent. From the purified product a salt is prepared with maleic acid in alcohol. The obtained 1.8 g (38%) of 9,10-dihydrolysergic-acid-(3'-/methylmercapto/)-anilide bimaleate melts at 174°–176° C. $/\alpha/_D^{20} = -60$ (c = 0.5, in 50% aqueous ethanol).

What we claim is:

1. 9,10-dihydrolysergic acid-(3'-/pyrrolid-2"-on-1'-yl/-propyl)-amide.

2. 1-methyl-9,10-dihydrolysergic acid-(thiazoline-2'-yl)-amide.

* * * * *